(12) United States Patent
De Weerdt

(10) Patent No.: US 12,385,999 B2
(45) Date of Patent: Aug. 12, 2025

(54) MRI WITH FAT/WATER SEPARATION

(71) Applicant: KONINKLIJKE PHILIPS N.V., Eindhoven (NL)

(72) Inventor: Elwin De Weerdt, Tilburg (NL)

(73) Assignee: Koninklijke Philips N.V., Eindhoven (NL)

( * ) Notice: Subject to any disclaimer, the term of this patent is extended or adjusted under 35 U.S.C. 154(b) by 929 days.

(21) Appl. No.: 16/965,038

(22) PCT Filed: Jan. 30, 2019

(86) PCT No.: PCT/EP2019/052279
§ 371 (c)(1),
(2) Date: Jul. 27, 2020

(87) PCT Pub. No.: WO2019/149769
PCT Pub. Date: Aug. 8, 2019

(65) Prior Publication Data
US 2021/0109177 A1  Apr. 15, 2021

(30) Foreign Application Priority Data
Feb. 2, 2018  (EP) .................... 18154840

(51) Int. Cl.
*G01R 33/48* (2006.01)
*A61B 5/055* (2006.01)
*G01R 33/56* (2006.01)
(52) U.S. Cl.
CPC .......... *G01R 33/4828* (2013.01); *A61B 5/055* (2013.01); *G01R 33/5607* (2013.01); *G01R 33/5608* (2013.01)
(58) Field of Classification Search
CPC ............ G01R 33/4828; G01R 33/5607; G01R 33/5608; A61B 5/055
See application file for complete search history.

(56) References Cited

U.S. PATENT DOCUMENTS 8,115,485 B1  2/2012  Maier et al.
2003/0060697 A1  3/2003  Zhang et al.
(Continued)

FOREIGN PATENT DOCUMENTS

EP  2503348 A1  9/2012

OTHER PUBLICATIONS

Bernstein Handbook of Magnetic Pulses p. 857-887 (2004).
(Continued)

*Primary Examiner* — Rochelle D Turchen

(57) ABSTRACT

The invention relates to a magnetic resonance imaging system (100). The magnetic resonance imaging system (100) comprises a memory (134) and a processor (130). The memory (134) stores machine executable instructions (140), first pulse sequence commands (142) and second pulse sequence commands (144). Execution of the machine executable instructions (140) by the processor (130) causing the processor (130) to control the magnetic resonance imaging system (100) to acquire identifying magnetic resonance data (146) using the first pulse sequence commands (142). The identifying magnetic resonance data (146) identifies on a per voxel basis, whether the respective voxel is water or fat dominated. Imaging magnetic resonance data (148) is acquired using the second pulse sequence commands (144). A magnetic resonance image (150) is reconstructed using the imaging magnetic resonance data (148). The identifying magnetic resonance data (146) is used to determine on a per voxel basis, whether the imaging magnetic resonance data (148) used for the reconstruction is dominantly induced by water or fat.

20 Claims, 4 Drawing Sheets

Acquire pre-scan magnetic resonance data — 200

Acquire further magnetic resonance data — 202

Reconstruct magnetic resonance image — 204

(56) References Cited

U.S. PATENT DOCUMENTS

| | | | |
|---|---|---|---|
| 2006/0058634 A1 | 3/2006 | Ikezaki | |
| 2010/0072998 A1 | 3/2010 | Hughes | |
| 2010/0244830 A1 | 9/2010 | Geppert et al. | |
| 2010/0283463 A1 | 11/2010 | Lu et al. | |
| 2013/0249553 A1 | 9/2013 | Simonetti et al. | |
| 2016/0124064 A1 | 5/2016 | De Weerdt et al. | |
| 2016/0313422 A1* | 10/2016 | Boernert | G01R 33/4828 |
| 2016/0313423 A1 | 10/2016 | Eggers | |
| 2017/0363699 A1* | 12/2017 | Ookawa | G01R 33/543 |
| 2018/0286041 A1* | 10/2018 | Hu | G06T 11/005 |

OTHER PUBLICATIONS

Rambow Olen et al: "Direct water and fat determination in two-point Dixon imaging with flexible echo times", Medical Physics, AIP, Melville, NY, US, vol. 40, No. 11, 112302, Oct. 11, 2013.

Houchun H. Hu et al: "Quantification of absolute fat mass using an adipose tissue reference signal model", Journal of Magnetic Resonance Imaging, vol. 28, No. 6, Aug. 21, 2008 (Aug. 21, 2008), pp. 1483-1491.

International Search Report and Written Opinion from PCT/EP2019/052279 mailed May 6, 2019.

\* cited by examiner

IR time = 50ms

IR time = 75ms

IR time = 100ms

MRI WITH FAT/WATER SEPARATION

CROSS REFERENCE TO RELATED APPLICATIONS

This application is a U.S. national phase application of International Application No. PCT/EP2019/052279 filed on Jan. 30, 2019, which claims the benefit of EP Application Serial No. 18154840.5 filed on Feb. 2, 2018 and is incorporated herein by reference.

FIELD OF THE INVENTION

The invention relates to magnetic resonance imaging, in particular to Dixon magnetic resonance imaging.

BACKGROUND OF THE INVENTION

A large static magnetic field is used by Magnetic Resonance Imaging (MRI) scanners to align the nuclear spins of atoms as part of the procedure for producing images within the body of a patient. This large static magnetic field is referred to as the B0 field.

During an MRI scan, Radio Frequency (RF) pulses generated by a transmitter coil cause perturbations to the local magnetic field, and RF signals emitted by the nuclear spins are detected by a receiver coil. These RF signals are used to construct the MRI images. These coils can also be referred to as antennas. Further, the transmitter and receiver coils can also be integrated into a single transceiver coil that performs both functions. It is understood that the use of the term transceiver coil also refers to systems where separate transmitter and receiver coils are used. The transmitted RF field is referred to as the B1 field.

MRI scanners are able to construct images of either slices or volumes. A slice is a thin volume that is only one voxel thick. A voxel is a small volume over which the MRI signal is averaged, and represents the resolution of the MRI image. A voxel may also be referred to as a pixel herein.

Dixon methods of magnetic resonance imaging include a family of techniques for producing separate water and lipid (fat) images. The various Dixon techniques such as, but not limited to, two-point Dixon methods, three-point Dixon methods, and six-point Dixon methods are collectively referred to herein as Dixon techniques or methods. The reconstruction of the water and fat images requires an adequate handling of the phase error, largely due to B0 inhomogeneity, to prevent swapping of water and fat signals.

The terminology to describe the Dixon techniques is well known and has been the subject of many review articles and is present in standard texts on Magnetic Resonance Imaging. For example, the "Handbook of MRI Pulse Sequences" by Bernstein et al., published by Elsevier Academic Press in 2004, contains a review of some Dixon techniques on pages 857 to 887.

SUMMARY OF THE INVENTION

The invention provides for a magnetic resonance imaging system, a computer program product, and a method in the independent claims. Embodiments are given in the dependent claims.

According to the invention the identifying magnetic resonance data represent the dominant chemical species, notably water or fat, in respective voxels in the subject being examined. In one implementation an identification map may be generated from the identifying magnetic resonance data. The identification map represents on a per voxel basis the dominant chemical species, in particular water or fat. The reconstruction of the magnetic resonance image from the imaging magnetic resonance data is done using the identification as an (a priori) constraint in the reconstruction. While the identification magnetic resonance data may be acquired before (as a pre-scan), during (e.g. interleaved with), or after the acquisition of the imaging magnetic resonance data, the identification map is available when reconstructing the magnetic resonance image. The use of a priori information on the dominant chemical species in respective voxels, notably water of fat (lipid), mitigates water-fat swaps in the reconstruction of the magnetic resonance image involving a water-fat separation, e.g. by way of a Dixon water-fat separation approach, The identifying magnetic resonance data may be acquired using the first pulse sequence commands that generate an identifying acquisition sequence that encodes the identifying magnetic resonance signals for the chemical species as well as a spatial encoding. An inversion recovery (IR) acquisition sequence is a suitable implementation of the first pulse sequence commands to acquire the identification magnetic resonance signals which contain an encoding of the dominant chemical species based on differences between longitudinal relaxation times $(T_1)$ In one aspect, the invention relates to a magnetic resonance imaging system. The magnetic resonance imaging system comprises a memory storing machine executable instructions, first pulse sequence commands and second pulse sequence commands. The first pulse sequence commands are configured to acquire identifying magnetic resonance data identifying on a per voxel basis, whether the respective voxel is water or fat dominated. The second pulse sequence commands are configured to acquire further magnetic resonance data. The magnetic resonance imaging system further comprises a processor for controlling the magnetic resonance imaging system. Execution of the machine executable instructions by the processor causing the processor to control the magnetic resonance imaging system to acquire the identifying magnetic resonance data using the first pulse sequence commands. Furthermore, the imaging magnetic resonance data is acquired using the second pulse sequence commands. A magnetic resonance image is reconstructed using the further magnetic resonance data. The identifying magnetic resonance data is used to determine on a per voxel basis, whether the imaging magnetic resonance data used for the reconstruction is dominantly induced by water or fat.

According to embodiments, the imaging magnetic resonance data comprise Dixon magnetic resonance data acquired using the second pulse sequence commands according to a Dixon magnetic resonance imaging protocol.

For example, a magnetic resonance imaging system for acquiring Dixon magnetic resonance data from an imaging zone is provided. Dixon magnetic resonance data is magnetic resonance data that has been acquired using a Dixon technique or protocol for magnetic resonance imaging. Dixon-type approaches for MRI, single point Dixon data acquisition as well as multi-point Dixon data acquisition, i.e. single-echo time as well as multi-echo time Dixon data acquisition, are techniques for water and fat separation. They may particularly be used for fat suppression in MRI images.

When performing magnetic resonance imaging, there may be phase errors which are introduced due to induced eddy currents and other imperfections in the magnetic resonance imaging system. When performing imaging techniques such as a Dixon magnetic resonance imaging protocol making a mistake in the phase can result in water or fat regions being improperly identified resulting in an image artifact commonly referred to as a fat/water swap.

Embodiments may have the beneficial effect of providing a more robust water/fat separation, while avoiding water/fat swaps.

The original method suggested by Dixon was based on acquiring two separate magnetic resonance images with a modified spin echo pulse sequence. One of the two images is a conventional spin echo image with water and fat signals in-phase, while for the other image magnetic resonance data is acquired using a readout gradient slightly shifted such that the water and fat signals are 180° out-of-phase. From these two images, a water-only image and a fat-only image can be generated. The water-only image may be used for fat suppression which us an important and widely used imaging option for clinical MRI.

However, Dixon-type methods still have limitations. Inherent to all Dixon methods is an artifact that causes fat/water swaps due to a natural ambiguity in the phase encoding and convergence of the employed optimization methods to local minima. In this case, mathematical computations may converge to a wrong substance, i.e. producing a fat-only image when a water-only image is desired. This phenomenon is referred to water/fat swapping. Water/fat swapping may particularly occur in highly inhomogeneous areas like the neck and around metal hardware.

Thus, Dixon approaches are e.g. sensitive to B0 inhomogeneities that may result in water/fat swapping in the image. Water/fat swapping occurs because B0 inhomogeneities create a natural ambiguity, when only one chemical species, i.e. water or fat, dominates the signal from a voxel. In this case, a fat signal is indistinguishable from a water signal. In other words, a correct signal intensity and thus image intensity may unambiguously be determined. However, it may remain unclear whether the respective signal intensity is caused by water or fat. Consequently, the success of a water/fat separation method largely depends on its ability to avoid such water/fat swaps.

Such B0 inhomogeneities may appear as phase errors in the acquired Dixon images. Without proper phase correction, the simple summation and subtraction approach as originally proposed by Dixon results in an incomplete water and fat separation, thus making the Dixon techniques sensitive to the magnetic field inhomogeneity.

For example, the in-phase signal $S_{in}$ comprises the sum of the water signal $S_{water}$ and the fat signal $S_{fat}$, while out-of-phase signal $S_{out}$ comprises the difference of the water signal $S_{water}$ and the fat signal $S_{fat}$. One may use absolute values of the signals in order to consider intensities only, i.e. $|S_{in}|=|S_{water}+S_{fat}|=S_{water}+S_{fat}$. However, in case of the $S_{out}$ an ambiguity remains: $|S_{in}|=|S_{water}-S_{fat}|=S_{water}-S_{fat}|$ if $S_{water}>S_{fat}$ or $|S_{in}|=|S_{water}-S_{fat}|=S_{fat}-S_{water}$ if $S_{fat}>S_{water}$.

Absolute values only provide information regarding the magnitude of the largest component of a voxel. Thus, additional information is required in order to determine, whether the respective largest component is fat or water. There are a number of different complex techniques discussed in the prior art to solve this problem. For example, a plurality of spin echoes may be used in multi-point Dixon techniques. However, even these multi-point Dixon are remaining subject to similar problems. Thus, all Dixon-based fat suppression sequences have to use some sophisticated algorithm to make an educated guess about water versus fat.

Taking the absolute values of the signals before summation or subtraction, the water and fat separation may actually already be correct on a voxel level without the need to know the actual phase errors. The real problem is rather in making a correct binary choice on whether the summed or the subtracted result corresponds to the water or fat on a voxel level.

According to embodiments, this information regarding the dominant chemical species is obtained via an additional scan, which e.g. is performed previous to the Dixon data acquisition and processing. Alternatively, it may be performed during the Dixon data acquisition and processing or even after the Dixon data acquisition. This additional scan is herein referred to as a 'pre-scan'. 'Pre-scan' is a label used herein to distinguish the respective data acquisition and/or the acquired data from the data acquisition using a Dixon protocol and/or the resulting 'Dixon' magnetic resonance data. According to embodiments, the identifying scan may comprise an inversion recovery spin echo based scan with an inversion time chosen such that at the time of excitation the fat is positive and water is negative or vice versa. This may result in fat dominant voxels having 180° opposite phase with respect to water dominant voxels in the final images. Because a spin-echo based sequence is used the phase in the final images is not influenced by B0 inhomogeneity. Therefore, it may become straight forward to identify which voxels are fat dominated and which ones are water dominated.

Pulse sequence commands as used herein encompass commands or data which may be converted into commands which are used for controlling the operation. 'Identifying scan' and 'Dixon' are labels used to distinguish different groups of data resulting from executing different groups of pulse sequence commands.

This general shortcoming of Dixon-type approaches, i.e. the requirement of preventing water/fat swaps, may be solved if it is known which voxels are 'fat' dominant, i.e. in which there is more fat than water, and which ones are 'water' dominant, i.e. in which there is more water than fat. This information provided by the pre-scan data may subsequently be used to resolve the Dixon ambiguity problem and hence leading to images without water/fat swaps even in challenging situations, like e.g. large FOV or isolated body parts. In other words, the identifying scan information may allow to find a correct B0 field map for the Dixon approach.

The identification of fat and water dominated voxels may be performed per voxel, without requiring additional information from other voxels. Consequently, a correct identification may be performed even in the case of isolated body parts within the FOV.

According to embodiments, the magnetic resonance image is a fat suppressed water image reconstructed using a water signal calculated from the Dixon magnetic resonance data. According to embodiments, the magnetic resonance image is a water suppressed fat image reconstructed using a fat signal calculated from the Dixon magnetic resonance data.

According to embodiments, the acquisition of the identifying magnetic resonance data is executed before the acquisition of the Dixon magnetic resonance data.

According to embodiments, the acquisition of the identifying magnetic resonance data is executed during the acquisition of the Dixon magnetic resonance data.

According to embodiments, the acquisition of the identifying magnetic resonance data is executed after the acquisition of the Dixon magnetic resonance data.

Embodiments May Comprise the Following Workflow:

Acquiring magnetic resonance data by a identifying scan identifying for each of the voxels the dominant chemical species, i.e. water or fat;

Performing a Dixon magnetic resonance data acquisition;

Reconstruct a fat or a water only image using the Dixon magnetic resonance data, in case of phase ambiguities use the information regarding the dominant chemical species per voxel to resolve the same.

Alternatively, the acquisition of the data may be included in the Dixon scans. As an example, one can add one additional acquisition of lower resolution with inversion pulse to two-point Dixon turbo spin echo (Dixon-TSE) scan resulting in a 2.5-point Dixon-TSE. In other words, the 'identifying scan' may be executed before the Dixon magnetic data acquisition or during the Dixon magnetic data acquisition.

According to embodiments, the Dixon protocol is a single-point Dixon protocol.

According to embodiments, the Dixon protocol is a multi-point Dixon protocol.

According to embodiments, the first pulse sequence commands are configured to acquire the identifying magnetic resonance data using an inversion recovery spin echo sequence.

An inversion recovery spin echo based scan may be used for determining which voxels are fat dominant, i.e. have more fat tissue than water tissue within, and which ones are water dominant, i.e. have more water than fat tissue within.

According to embodiments, the inversion recovery spin echo sequence is an inversion recovery turbo spin echo.

An inversion recovery (IR) spin echo sequence refers to a spin echo (SE) pulse sequence preceded by a 180° RF pulse. A spin echo sequences in general comprises a slice selective 90°-pulse followed by one or more 1800 refocusing pulses. In other words, a SE sequence may be denoted as {90°-180°-echo}, while an IR sequence may be provided as 180°-{90°-180°-echo}. The time between the 180° inverting pulse and the 90°-pulse is called the inversion time (TI). The repetition time (TR) and echo time (TE) are defined as they are for spin echo. Due to the 180° inverting pulse an initial longitudinal magnetization MO of all tissues, i.e. chemical species, are inverted to an opposite orientation in relation to main magnetic field B0. During the TI interval, these inverted chemical species undergo T1 relaxation seeking to re-establish magnetization along the +z-direction. When the spin echo signal generation begins, i.e. at the 90°-pulse, the initial longitudinal magnetizations of different chemical species are separated depending on their different intrinsic T1 relaxation times. The degree of separation and hence the resulting image contrast may be controlled by varying the TI parameter in the IR spin echo pulse sequence. Additional contrast effects may be obtained by varying TR and/or TE.

A TSE pulse sequence resembles a standard spin-echo pulse sequence in that it uses a series of 180°-refocusing pulses after a single 90°-pulse to generate a train of echoes. In shorthand notation a standard SE pulse sequence may be provided as {90°-180°-echo}, while a TSE pulse sequence may take the form {90°-180°-echo-180°-echo-180°-echo-180°-echo . . . }. An inversion recovery turbo spin echo may be provided by 180°-{90°-180°-echo-180°-echo-180°-echo-180°-echo . . . }. Using a TSE pulse sequence, the phase-encoding gradient for each of the echoes are changed, while a standard multi-echo sequence collects all echoes in a train with the same phase encoding. As a result of changing the phase-encoding gradient between echoes, multiple lines of k-space, i.e. phase-encoding steps, can be acquired within a given repetition time using a TSE pulse sequence.

According to embodiments, the spin echo inversion recovery type identifying scan is performed, wherein the inversion time causes different phases for water and fat dominated voxels. The inversion time is set such that during RF excitation fat is positive, while water is negative (or vice versa) for the pre-scan. This, phase difference allows to identify water and fat dominated voxels, respectively. From the magnetic resonance signals acquired in a subsequent Dixon acquisition sequence, in particular a multi-echo time Dixon acquisition sequence, water and fat separation is done with the use of the information from the identifying scan. Since it is known from the identifying scan data, which voxels are water dominated and which voxels are water dominated, the general phase ambiguities of the Dixon approach may easily be resolved and water/fat swaps prevented.

In case of a spin-echo based sequence, the phase in the final images may not influenced by B0 inhomogeneitis. Spin-echo based sequences generally comprise a 90°-pulse and a subsequent 180°-pulse. The 90°-pulse first tips these spins into the transverse plane. Because the local microscopic fields may differ slightly, some spin groups may precess faster and gain phase relative to others. The 180°-pulse turns the entire system on its head. After this flip, the faster precessing spins with continued evolution eventually catch up with the slower spins. This occurs at time corresponding to the center of the spin echo. Beyond the echo center the faster spins once again leave the slower ones behind resulting a dephasing of the system.

The 180°-pulse of spin-echo based sequences results in a refocusing of nonmoving spins whose phases have been scattered by constant field distortions and inhomogeneities. Thus, the 180°-pulse may correct for imperfections in the main magnetic field, i.e. B0 field, of any cause.

According to embodiments, a resolution of the identifying magnetic resonance data is lower than a resolution of the Dixon magnetic resonance data. According to embodiments, it may be sufficient, when the information regarding the dominant chemical species per voxel is provided by the pre-scan on a coarser resolution, e.g. approx. 5 to 10 mm, than the resolution used for the Dixon approach.

According to embodiments, a resolution of the identifying magnetic resonance data equal to the resolution of the Dixon magnetic resonance data may be generated by interpolated and used for processing the Dixon magnetic resonance data.

In another aspect, the invention relates to a method for controlling a magnetic resonance imaging system. The magnetic resonance imaging system comprises a memory and a procesor. The memory stores machine executable instructions, first pulse sequence commands and second pulse sequence commands. The first pulse sequence commands are configured to acquire identifying magnetic resonance data identifying on a per voxel basis, whether the respective voxel is water or fat dominated. The second pulse sequence commands are configured to acquire further magnetic resonance data. Execution of the machine executable instructions by the processor causing the processor to control the magnetic resonance imaging system to execute the method. The method comprises acquiring the identifying magnetic resonance data using the first pulse sequence commands. The imaging magnetic resonance data is acquired using the second pulse sequence commands. A magnetic resonance image is reconstructed using the further magnetic resonance data. The identifying magnetic resonance data is used to determine on a per voxel basis, whether the imaging magnetic resonance data used for the reconstruction is dominantly induced by water or fat.

According to embodiments, the imaging magnetic resonance data comprise Dixon magnetic resonance data acquired using the second pulse sequence commands according to a Dixon magnetic resonance imaging protocol.

According to embodiments, the reconstructed image is one or more of the following: a fat suppressed image, a water suppressed image, or a mixed water/fat image (e.g. so called in-phase or out-phase image).

According to embodiments, the first pulse sequence commands are configured to acquire the identifying magnetic resonance data using an inversion recovery spin echo sequence.

In another aspect, the invention relates to a computer program product. The computer program product comprises machine executable instructions, first pulse sequence commands and second pulse sequence commands. The first pulse sequence commands are configured to acquire identifying magnetic resonance data identifying on a per voxel basis, whether the respective voxel is water or fat dominated. The second pulse sequence commands are configured to acquire further magnetic resonance data. Execution of the machine executable instructions by a processor controlling a magnetic resonance imaging system causes the processor to control the magnetic resonance imaging system to acquire the identifying magnetic resonance data using the first pulse sequence commands. The imaging magnetic resonance data is acquired using the second pulse sequence commands. A magnetic resonance image is reconstructed using the further magnetic resonance data. The identifying magnetic resonance data is used to determine on a per voxel basis, whether the imaging magnetic resonance data used for the reconstruction is dominantly induced by water or fat.

According to embodiments, the imaging magnetic resonance data comprise Dixon magnetic resonance data acquired using the second pulse sequence commands according to a Dixon magnetic resonance imaging protocol.

According to embodiments, the reconstructed image is one or more of the following: a fat suppressed image, a water suppressed image, or a mixed water/fat image (e.g. so called in-phase or out-phase image).

According to embodiments, the first pulse sequence commands are configured to acquire the identifying magnetic resonance data using an inversion recovery spin echo sequence.

It is understood that one or more of the aforementioned embodiments of the invention may be combined as long as the combined embodiments are not mutually exclusive.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example, a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object-oriented programming language such as Java, Smalltalk, C++ or the like and conventional procedural programming languages, such as the "C" programming language or similar programming languages and compiled into machine executable instructions. In some instances, the computer executable code may be in the form of a high-level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance (MR) data is defined herein as being the recorded measurements of radio frequency signals emitted by atomic spins using the antenna of a Magnetic resonance apparatus during a magnetic resonance imaging scan. A Magnetic Resonance Imaging (MRI) image or MR image is defined herein as being the reconstructed two or three-dimensional visualization of anatomic data contained within the magnetic resonance imaging data. This visualization can be performed using a computer.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
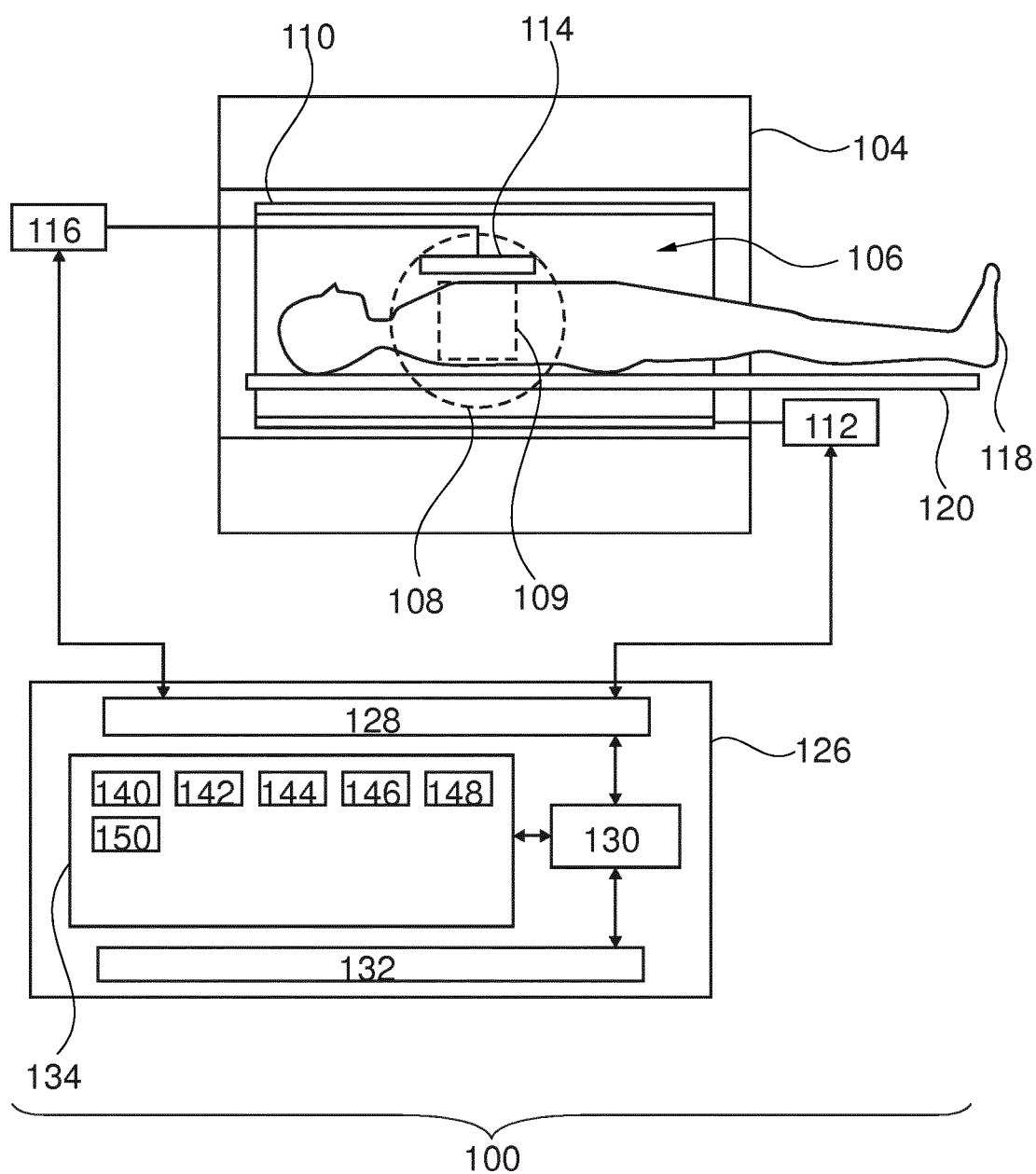
FIG. 1 illustrates an example of a magnetic resonance imaging system.

FIG. 1 shows an example of a magnetic resonance imaging system 100 with a magnet 104. The magnet 104 is a superconducting cylindrical type magnet with a bore 106 through it. The use of different types of magnets is also possible. For instance, it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 106 of the superconducting cylindrical type magnet 104 there is an imaging zone 108 where the magnetic field is strong and uniform enough to perform magnetic resonance imaging. A region of interest 109 is shown within the imaging zone 108. The magnetic resonance data is typically acquired for the region of interest. A subject 118 is shown as being supported by a subject support 120 such that at least a portion of the subject 118 is within the imaging zone 108 and the region of interest 109.

Within the bore 106 of the magnet there is also a set of magnetic field gradient coils 110 which is used for acquisition of magnetic resonance data to spatially encode magnetic spins within the imaging zone 108 of the magnet 104. The magnetic field gradient coils 110 are connected to a magnetic field gradient coil power supply 112. The magnetic field gradient coils 110 are intended to be representative. Typically, magnetic field gradient coils 110 contain three separate sets of coils for spatially encoding in three orthogonal spatial directions. A magnetic field gradient power supply supplies current to the magnetic field gradient coils. The current supplied to the magnetic field gradient coils 110 is controlled as a function of time and may be ramped or pulsed.

Adjacent to the imaging zone 108 is a radio-frequency coil 114 for manipulating the orientations of magnetic spins within the imaging zone 108 and for receiving radio transmissions from spins also within the imaging zone 108. The radio frequency antenna may contain multiple coil elements. The radio frequency antenna may also be referred to as a channel or antenna. The radio-frequency coil 114 is connected to a radio frequency transceiver 116. The radio-frequency coil 114 and radio frequency transceiver 116 may be replaced by separate transmit and receive coils and a separate transmitter and receiver. It is understood that the radio-frequency coil 114 and the radio frequency transceiver 116 are representative. The radio-frequency coil 114 is intended to also represent a dedicated transmit antenna and a dedicated receive antenna. Likewise, the radio frequency transceiver 116 may also represent a separate transmitter and separate receivers. The radio-frequency coil 114 may also have multiple receive/transmit elements and the radio frequency transceiver 116 may have multiple receive/transmit channels. For example, if a parallel imaging technique such as SENSE is performed, the radio-frequency coil 114 will have multiple coil elements.

The radio frequency transceiver 116 and the magnetic field gradient coil power supply 112 are shown as being connected to a hardware interface 128 of a computer system 126. The computer system further comprises a processor 130 that is in communication with the hardware interface 128, a memory 134, and a user interface 132. The memory 134 may be any combination of memory which is accessible to the processor 130. This may include such things as main memory, cached memory, and also non-volatile memory such as flash RAM, hard drives, or other storage devices. In some examples the memory 134 may be considered to be a non-transitory computer-readable medium.

The memory 134 is shown as containing machine-executable instructions 140. The machine-executable instructions 140 enable the processor 130 to control the operation and function of the magnetic resonance imaging system 100. The machine-executable instructions 140 may also enable the processor 130 to perform various data analysis and calculation functions. The memory 134 is further shown as containing first pulse sequence commands 142.

The first pulse sequence commands 142 are configured for controlling the magnetic resonance imaging system 100 to acquire pre-scan identifying magnetic resonance data 146 from the subject identifying on a per voxel basis, whether the respective voxel is water or fat dominated. The first pulse sequence commands 142 may be configured to acquire the pre-scan identifying magnetic resonance data 146 using an inversion recovery spin echo sequence.

The memory 134 is further shown as containing second pulse sequence commands 144. The second pulse sequence commands 144 are configured for controlling the magnetic resonance imaging system 100 to acquire imaging magnetic resonance data from the subject, e.g. Dixon magnetic resonance data 148 according to a Dixon magnetic resonance imaging protocol.

The first pulse sequence commands 142 may be executed before execution of the second pulse sequence commands 144 or during execution of the second pulse sequence commands 144. According to embodiments, the first pulse sequence commands 142 may even be executed after execution of the second pulse sequence commands 144.

The memory 134 is further shown as containing the pre-scan identifying magnetic resonance data 146 acquired executing the first pulse sequence commands 142 and the Dixon magnetic resonance data 148 acquired executing the second pulse sequence commands 144.

The memory 134 is further shown as containing a magnetic resonance image 150 reconstructed using the Dixon magnetic resonance data 148. The pre-scan identifying magnetic resonance data 146 is used to determine on a per voxel basis, whether the Dixon magnetic resonance data 148 used for the reconstruction is dominantly induced by water or fat. According to embodiments, the magnetic resonance image 150 may be a fat supressed water image or a water supressed fat image. According to embodiments, fat supressed water image and a water supressed fat image may be reconstructed and comprised memory 134.

Figure 2:
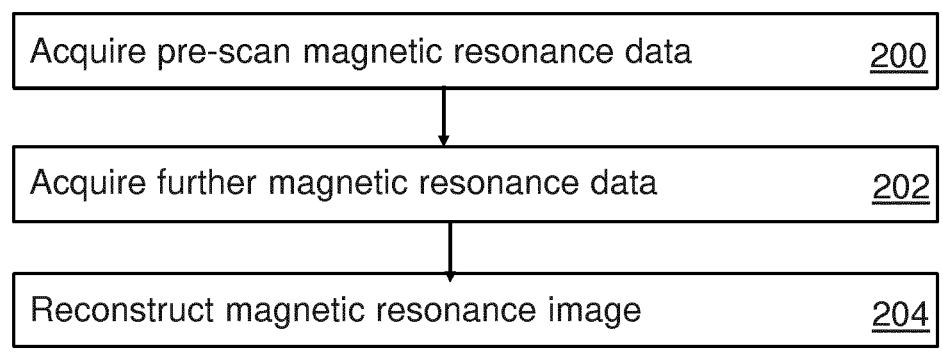
FIG. 2 shows a flow chart which illustrates a method of operating the magnetic resonance imaging system of claim 1.

FIG. 2 shows a flowchart which illustrates a method of operating the magnetic resonance imaging system 100 of FIG. 1. In step 200 the magnetic resonance imaging system 100 is controlled with the first pulse sequence commands 142 to acquire the pre-scan identifying magnetic resonance data 146. In step 202 the magnetic resonance imaging system 100 is controlled with the second pulse sequence commands 144 to acquire further magnetic resonance data, e.g. Dixon magnetic resonance data 148. According to embodiments, step 200 may be executed before step 202, during step 202 or after step 202. In step 204 the Dixon magnetic resonance data 148 acquired in step 204 is used for reconstructing the magnetic resonance image 150. The magnetic resonance image 150 may be a fat suppressed or a water suppressed image or a mixed water/fat image (e.g. so called in-phase or out-phase image). According to embodiments, a fat suppressed or a water suppressed image or a mixed water/fat image (e.g. so called in-phase or out-phase image) are reconstructed. The pre-scan identifying magnetic resonance data 146 is used to determine on a per voxel basis, whether the Dixon magnetic resonance data 148 used for the reconstruction is dominantly induced by water or fat, and thus resolve phase ambiguities of the Dixon approach.

Figure 3A:
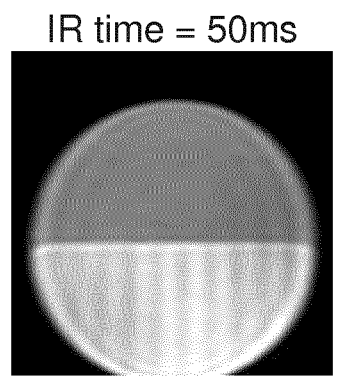
FIG. 3 shows examples of intensity magnetic resonance images.
Figure 3B:
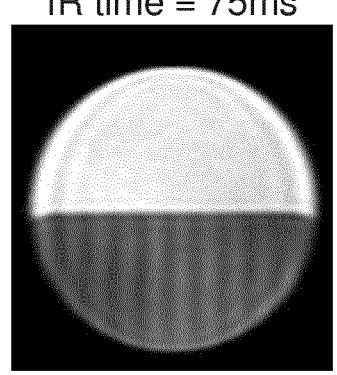
Figure 3C:
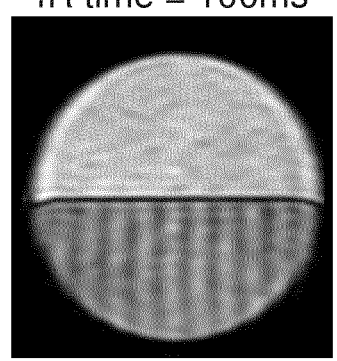
Figure 4A:
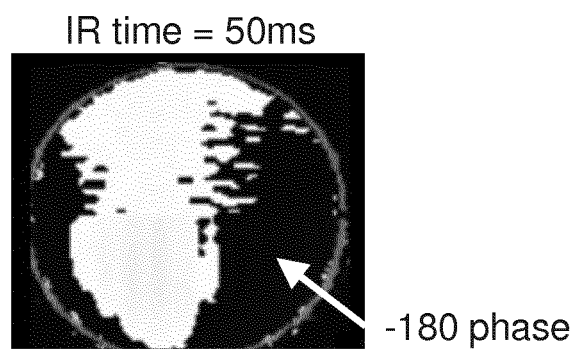
FIG. 4 shows examples of phase magnetic resonance images.
Figure 4B:
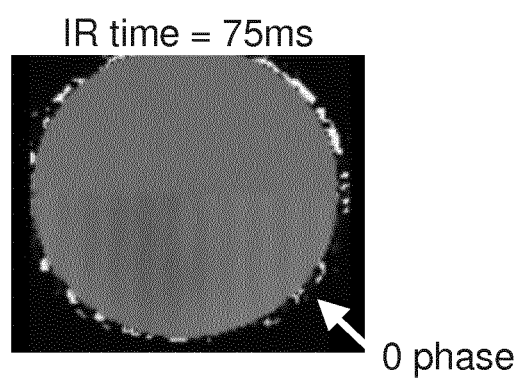
Figure 4C:
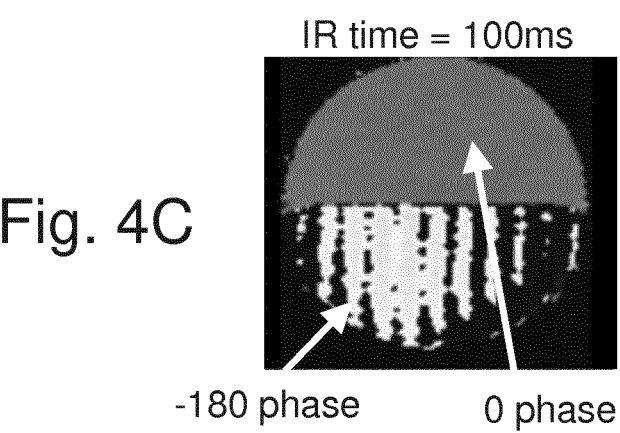

FIGS. 3A-C show examples of magnetic resonance images demonstrating magnitude, i.e. intensity, behavior of exemplary doped water and sunflower fat with respect to inversion time (IR) of an examplary inversion recovery spin echo sequence of a pre-scan. The inversion recovery spin echo sequence comprises a standard spin echo sequence. FIGS. 4A-C show examples of magnetic resonance images demonstrating phase behavior of the exemplary doped water and sunflower fat depicted in FIGS. 3A-C. For IR 50 ms a clear π/πrad=180° phase difference between water and fat is obtained. Based on this phase difference, it can be identified which of the voxels are water dominated (π) and which are fat dominated (−π). For IR 75 ms no phase difference is seen, i.e. the gray indicates 0°. For 100 ms a clear π/πrad=180° phase difference between water and fat is only optained for half of the depicted sample, while the other half desplays no phase difference.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 magnetic resonance imaging system
104 magnet
106 bore of magnet
108 imaging zone
109 region of interest
110 magnetic field gradient coils
112 magnetic field gradient coil power supply
114 radio-frequency coil
116 transceiver
118 subject
120 subject support
126 computer system
128 hardware interface
130 processor
132 user interface
134 computer memory
140 machine executable instructions
142 first pulse sequence commands
144 second pulse sequence commands
146 pre-scan magnetic resonance data
148 Dixon magnetic resonance data
150 magnetic resonance image

The invention claimed is:

1. A magnetic resonance imaging system, the magnetic resonance imaging system comprising:
  a memory storing machine executable instructions, first pulse sequence commands and second pulse sequence commands, wherein the first pulse sequence commands are configured to acquire identifying magnetic resonance data identifying dominant chemical species in respective voxels, wherein the second pulse sequence commands are configured to acquire imaging magnetic resonance data, and wherein the dominant chemical species comprise water or fat;
  a processor for controlling the magnetic resonance imaging system, execution of the machine executable instructions by the processor causing the processor to control the magnetic resonance imaging system to:
    acquire the identifying magnetic resonance data using the first pulse sequence commands that are configured to acquire the identifying magnetic resonance data using an inversion recovery spin echo sequence, which causes a phase difference between water dominated voxels and fat dominated voxels of the respective voxels;
    identify the water dominated voxels and the fat dominated voxels from the identifying magnetic resonance data based on the phase difference;
    acquire the imaging magnetic resonance data using the second pulse sequence commands, wherein the imaging magnetic resonance data includes phase errors that cause ambiguities regarding portions of the imaging magnetic resonance data being dominantly introduced by water or fat; and
    reconstruct a magnetic resonance image using the imaging magnetic resonance data, wherein reconstructing the magnetic resonance image comprises determining on a per voxel basis whether the image magnetic resonance data used for the reconstruction of the magnetic resonance image is dominantly induced by water or fat using the dominant chemical species in the respective voxels identified from the identifying magnetic resonance data, thereby preventing swaps of water regions and fat regions in the reconstruction of the magnetic resonance image caused by the ambiguities in the imaging magnetic resonance data.

2. The magnetic resonance imaging system of claim 1, wherein the imaging magnetic resonance data comprise Dixon magnetic resonance data acquired using the second pulse sequence commands according to a Dixon magnetic resonance imaging protocol.

3. The magnetic resonance imaging system of claim 2, wherein the Dixon magnetic resonance imaging protocol is one of a single-point Dixon protocol or a multi-point Dixon protocol.

4. The magnetic resonance imaging system of claim 1, wherein the reconstructed magnetic resonance image is at least one a fat suppressed image, a water suppressed image, or a mixed water/fat image.

5. The magnetic resonance imaging system of claim 1, wherein the acquisition of the identifying magnetic resonance data is executed as a pre-scan before the acquisition of the imaging magnetic resonance data.

6. The magnetic resonance imaging system of claim 1, wherein the acquisition of the identifying magnetic resonance data is executed during the acquisition of the imaging magnetic resonance data.

7. The magnetic resonance imaging system of claim 1, wherein the acquisition of the identifying magnetic resonance data is executed after the acquisition of the imaging magnetic resonance data.

8. The magnetic resonance imaging system of claim 1, wherein a resolution of the identifying magnetic resonance data is lower than a resolution of the imaging magnetic resonance data.

9. A method for controlling a magnetic resonance imaging system comprising a memory storing machine executable instructions, first pulse sequence commands and second pulse sequence commands, and a processor for controlling the magnetic resonance imaging system upon execution of the machine executable instructions to execute the method comprising:
  acquiring identifying magnetic resonance data using the first pulse sequence commands, wherein the identifying magnetic resonance data identifies whether voxels are water dominated or fat dominated on a per voxel basis, and wherein the first pulse sequence commands are configured to acquire the identifying magnetic resonance data using an inversion recovery spin echo sequence, which causes a phase difference between water dominated voxels and fat dominated voxels;
  acquiring imaging magnetic resonance data using the second pulse sequence commands, wherein the imaging magnetic resonance data includes phase errors that cause ambiguities regarding portions of the imaging magnetic resonance data being dominantly introduced by water or fat; and
  reconstructing a magnetic resonance image using the imaging magnetic resonance data, wherein reconstructing a magnetic resonance image comprises determining, on a per voxel basis, whether the imaging magnetic resonance data used for the reconstruction is dominantly induced by water or fat using the identifying magnetic resonance data, and wherein the determination of whether the imaging magnetic resonance data is dominantly induced by water or fat is used to prevent swaps of water regions and fat regions in the reconstruction of the magnetic resonance image otherwise resulting from the ambiguities in the imaging magnetic resonance data.

10. The method of claim 9, wherein the imaging magnetic resonance data comprise Dixon magnetic resonance data acquired using the second pulse sequence commands according to a Dixon magnetic resonance imaging protocol.

11. A tangible, non-transitory computer readable medium that stores executable instructions, first pulse sequence commands and second pulse sequence commands, wherein the first pulse sequence commands are configured to acquire identifying magnetic resonance data identifying whether voxels are water or fat dominated, on a per voxel basis, wherein the second pulse sequence commands are configured to acquire imaging magnetic resonance data, wherein execution of the executable instructions by a processor causes the processor to control a magnetic resonance imaging system to:
  acquire the identifying magnetic resonance data using the first pulse sequence commands that are configured to acquire the identifying magnetic resonance data using an inversion recovery turbo spin echo sequence which causes a phase difference between water dominated voxels and fat dominated voxels;
  identify the water dominated voxels and the fat dominated voxels from the identifying magnetic resonance data based on the phase difference;
  acquire the imaging magnetic resonance data using the second pulse sequence commands, wherein the imaging magnetic resonance data includes phase errors that cause ambiguities regarding portions of the imaging magnetic resonance data being dominantly introduced by water or fat; and
  reconstruct a magnetic resonance image using the imaging magnetic resonance data, wherein reconstructing the magnetic resonance image comprises determining on a per voxel basis whether the image magnetic resonance data used for the reconstruction of the magnetic resonance image is dominantly induced by water or fat using the identifying magnetic resonance data, thereby preventing swaps of water regions and fat regions in the reconstruction of the magnetic resonance image caused by the ambiguities in the imaging magnetic resonance data.

12. The tangible, non-transitory computer readable medium of claim 11, wherein the imaging magnetic resonance data comprise Dixon magnetic resonance data acquired using the second pulse sequence commands according to a Dixon magnetic resonance imaging protocol.

13. The tangible, non-transitory computer readable medium of claim 12, wherein the Dixon magnetic resonance imaging protocol is one of a single-point Dixon protocol or a multi-point Dixon protocol.

14. The tangible, non-transitory computer readable medium of claim 11, wherein the reconstructed magnetic resonance image is at least one of a fat suppressed image, a water suppressed image, or a mixed water/fat image.

15. The tangible, non-transitory computer readable medium of claim 11, wherein the acquisition of the identifying magnetic resonance data is executed as a pre-scan before the acquisition of the imaging magnetic resonance data.

16. The tangible, non-transitory computer readable medium of claim 11, wherein the acquisition of the identifying magnetic resonance data is executed during the acquisition of the imaging magnetic resonance data.

17. The tangible, non-transitory computer readable medium of claim 11, wherein the acquisition of the identifying magnetic resonance data is executed after the acquisition of the imaging magnetic resonance data.

18. The tangible, non-transitory computer readable medium of claim 11, wherein a resolution of the identifying magnetic resonance data is lower than a resolution of the imaging magnetic resonance data.

19. The method of claim 10, wherein the Dixon magnetic resonance imaging protocol is one of a single-point Dixon protocol or a multi-point Dixon protocol.

20. The magnetic resonance imaging system of claim 1, wherein the first pulse sequence commands provide a turbo spin echo inversion recovery scan, and wherein inversion time of the turbo spin echo inversion recovery scan causes different phases for the water dominated voxels and the fat dominated voxels.

* * * * *